(12) United States Patent
Sawatzki et al.

(10) Patent No.: US 9,889,024 B2
(45) Date of Patent: Feb. 13, 2018

(54) COSMETIC PROSTHESIS COVER

(71) Applicant: OTTO BOCK HEALTHCARE GMBH, Duderstadt (DE)

(72) Inventors: Steffen Sawatzki, Sollstedt (DE); Markus Schneegans, Rollshausen (DE); Sven Zarling, Duderstadt (DE); Sandra Niederstrasser, Duderstadt (DE); Andreas Kruse, Worbis (DE); Ilka Schlesiger, Jena (DE); Christian Thomas, Jena (DE); Dirk Haase, Leipzig (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 14/361,246

(22) PCT Filed: Nov. 13, 2012

(86) PCT No.: PCT/EP2012/004709
§ 371 (c)(1),
(2) Date: May 28, 2014

(87) PCT Pub. No.: WO2013/079159
PCT Pub. Date: Jun. 6, 2013

(65) Prior Publication Data
US 2014/0371872 A1 Dec. 18, 2014

(30) Foreign Application Priority Data
Nov. 30, 2011 (DE) .......................... 10 2011 120 661

(51) Int. Cl.
*A61F 2/50* (2006.01)
*A61F 2/60* (2006.01)
(Continued)

(52) U.S. Cl.
CPC ........ *A61F 2/50* (2013.01); *A61F 2/60* (2013.01); *A61F 2002/5001* (2013.01); *D03D 3/02* (2013.01); *D03D 27/06* (2013.01)

(58) Field of Classification Search
CPC ........................ A61F 2002/5001; A61F 2/60
See application file for complete search history.

(56) References Cited

U.S. PATENT DOCUMENTS

| 5,133,775 A | 7/1992 | Chen |
| 5,385,036 A * | 1/1995 | Spillane .................. A43B 1/04 2/16 |

(Continued)

FOREIGN PATENT DOCUMENTS

| DE | 10040955 A1 | 3/2002 |
| DE | 20309318 U1 | 9/2003 |

(Continued)

OTHER PUBLICATIONS

PCT International Search Report for PCT International Patent Application No. PCT/EP2012/004709, dated Feb. 27, 2013.

*Primary Examiner* — Marcia Watkins
(74) *Attorney, Agent, or Firm* — Holland & Hart

(57) ABSTRACT

The invention relates to a cosmetic cover (1) for lining a prosthesis (10), with a distal section (2), and with a joint section (3) which, when the cosmetic cover (1) for the prosthesis is fitted in place, covers a joint mechanism (30) arranged between a proximal prosthesis component (40) and a distal prosthesis component (20), wherein the joint section (3) is made from a 3D spacer knit having an upper textile and a lower textile, which are spaced apart and attached to each other by support threads.

16 Claims, 7 Drawing Sheets

(51) Int. Cl.
*D03D 27/06* (2006.01)
*D03D 3/02* (2006.01)

(56) References Cited

U.S. PATENT DOCUMENTS

| | | | |
|---|---|---|---|
| 5,659,895 A * | 8/1997 | Ford, Jr. | A62B 17/008 |
| | | | 2/2.11 |
| 6,037,035 A | 3/2000 | Bottger | |
| 6,652,596 B2 * | 11/2003 | Smith | A61F 2/60 |
| | | | 2/22 |
| 7,090,651 B2 | 8/2006 | Chiang et al. | |
| 7,762,973 B2 | 7/2010 | Einarsson et al. | |
| 8,726,422 B1 * | 5/2014 | Pirela | A41B 11/14 |
| | | | 2/242 |
| 2006/0173553 A1 | 8/2006 | Holzer et al. | |
| 2007/0185425 A1 | 8/2007 | Einarsson et al. | |
| 2007/0225824 A1 | 9/2007 | Einarsson | |
| 2008/0021363 A1 * | 1/2008 | Fee | A41D 13/0562 |
| | | | 602/76 |
| 2009/0192532 A1 * | 7/2009 | Spinnler | A61F 2/0063 |
| | | | 606/153 |
| 2010/0130903 A1 * | 5/2010 | Rock | 602/62 |
| 2010/0192269 A1 * | 8/2010 | Saranga | A41D 13/065 |
| | | | 2/24 |
| 2010/0318195 A1 | 12/2010 | Kettwig et al. | |
| 2012/0034833 A1 | 2/2012 | Schaube et al. | |
| 2012/0283846 A1 | 11/2012 | Janssen et al. | |

FOREIGN PATENT DOCUMENTS

| | | |
|---|---|---|
| DE | 102007035409 B4 | 6/2010 |
| DE | 202009006966 U1 | 10/2010 |
| DE | 102009051441 A1 | 5/2011 |
| EP | 0985388 A2 | 3/2000 |
| WO | 2005009304 A1 | 2/2005 |
| WO | 2009115835 A1 | 9/2009 |
| WO | 2011050894 A2 | 5/2011 |

* cited by examiner

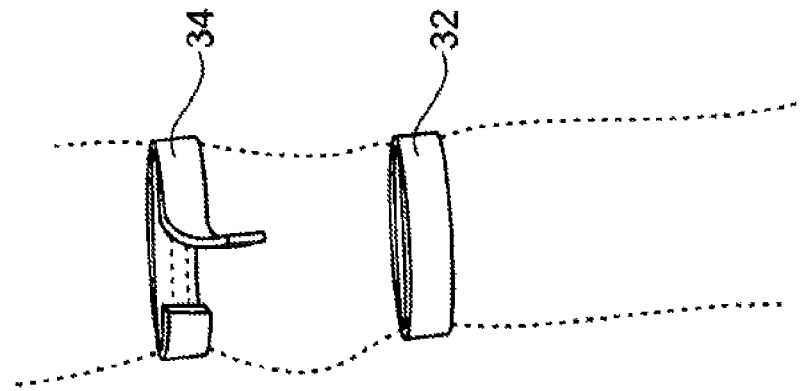
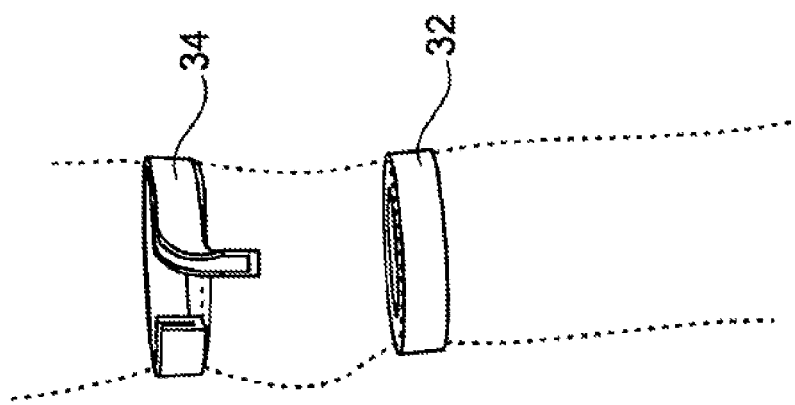
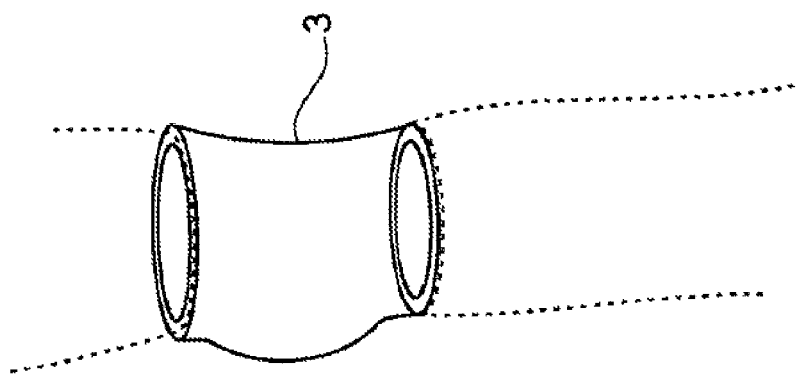

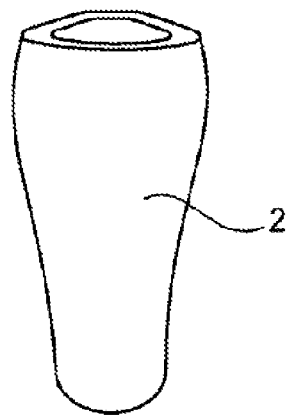
Fig. 11a
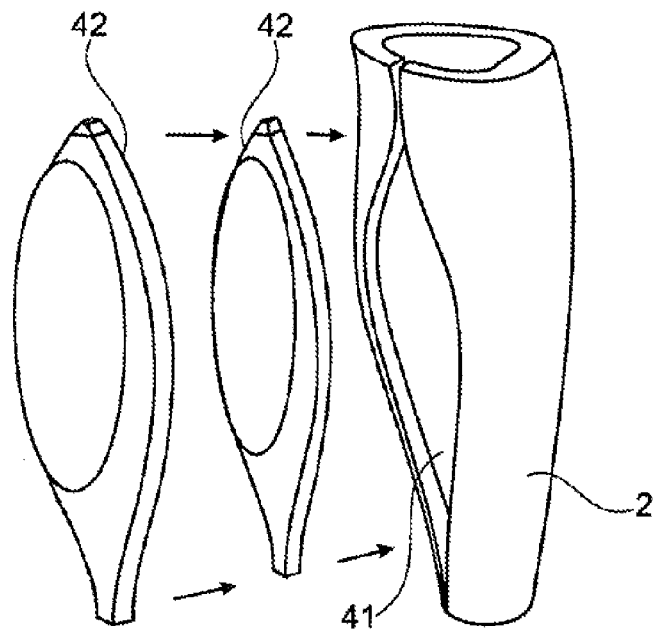
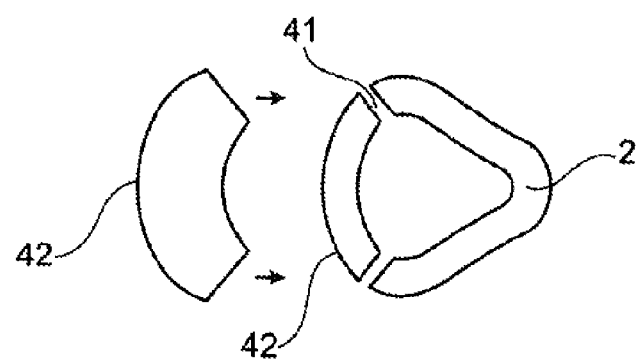
Fig. 11b

COSMETIC PROSTHESIS COVER

TECHNICAL FIELD

The invention relates to a cosmetic prosthesis cover for covering a prosthesis, having a distal portion and a joint portion which, in the fitted state of the cosmetic prosthesis cover, covers a joint unit which is disposed between a proximal prosthetic component and a distal prosthetic component. Such a cosmetic prosthesis cover is provided, in particular, for covering prosthetic legs, but may also be implemented in the case of a forearm prosthesis in which an elbow joint has to be covered.

BACKGROUND

Patients requiring prosthetic aid often wish for the prosthetic aid to be as inconspicuous as possible, wherein inconspicuousness relates to both functionality and visual appearance. In the case, for example, where it is necessary to replace parts of a leg above the knee, a prosthetic knee joint has to be provided in order to replace the functionality of the natural knee joint. This prosthetic knee joint is usually fastened on the patient by way of a thigh socket which receives the thigh stump. A lower leg, usually of tubular shape, via which a prosthetic foot is coupled to the prosthetic knee joint, is distally disposed on the prosthetic knee joint. In order to achieve a shape which approximates that of a natural leg, covering parts, in most cases of a foam material, which replicate the muscles of the lower leg, are disposed about the lower-leg tube. A casing of a skin-colored material may be pulled over the entire prosthetic aid consisting of prosthetic unit and covering, so that a comparatively inconspicuous prosthetic aid can also be achieved with respect to shaping.

U.S. Pat. No. 5,133,775 relates to a covering for an artificial limb made from a polyurethane foam which is configured so as to be semi-rigid. The covering extends over the entire artificial limb and, in the region of the prosthetic joint, has a multiplicity of slots which have a diamond shape and are disposed, spaced apart from one another, in rows and columns. The covering is configured in one piece.

WO 2005/009304 A1 relates to a lightweight prosthesis for the purely visual replacement of missing extremities, having a molding which replicates the missing extremity and a receptacle for connecting the prosthesis with the stump of the missing extremity. The molding consists of a lightweight plastic material and may contain one joint or a plurality of joints for replicating the joint or the joints, respectively, of the missing extremities. Reinforcement layers may be disposed on the inner side of the molding, on the flexion side and the extension side of the joints.

U.S. Pat. No. 7,090,651 A1 relates to a compressive orthosis having an elastic tubular structure, which was made from a blank of a composite material. The composite material has a first layer having an elastic, stretchable material with an inner surface and an outer surface. A flexible second layer with an outer surface which is fastened on the inner surface of the first layer, and a third layer, which is configured from a spacer warp-knit having an outer surface which is disposed on the inner surface of the second layer, and a flexible fourth layer, the outer side of which is fastened on the inner side of the third layer. A plurality of slots may be introduced in the first layer. The second and fourth layers are preferably configured from a knit. The third layer, which is configured as a spacer warp-knit, has two surfaces which are spaced apart from one another and which are also referred to as the base fabric and which are interconnected by way of a multiplicity of spacer threads. It is an object of the bandage to provide improved compression, to retain body heat and to achieve improved breathing activity.

U.S. Pat. No. 7,762,973 B2 describes a spacer element for the improved adaptation of an orthosis unit to the user. The spacer element may be a textile which is provided with a coating. The spacer element is disposed between the frame of the orthosis and the user of the orthosis.

DE 203 09 318 U1 relates to a knee-region separation adapter for the releasable connection of a first cosmetic foam part, which can be slid over a knee joint of a leg prosthesis and can be placed over a thigh stump, having a second cosmetic foam part into which a lower-leg part of the leg prosthesis can be incorporated.

Two plate-shaped adapter parts are provided, wherein a first adapter part is releasably connectable to the first cosmetic foam part, and a second adapter part to the second cosmetic foam part.

DE 100 40 955 A1 describes a cuff for shrouding a region of an artificial knee joint of a leg prosthesis. The cuff is substantially composed of an annular basic body of a flexible material. One end of the basic body can be placed on the thigh stump, the other end can be placed on the lower-leg prosthesis of the leg prosthesis. In the region of the knee joint, the cuff is configured as a bellows. In relation to the environment, the cuff forms a sealing element against dirt and water.

Problematic issues in the case of most cosmetic prosthesis covers include the high load in the joint region on account of the large deformations in the case of full flexion, together with high compression-related and expansion-related circumferences. In this manner, cracking arises in particular in the case of a cosmetic prosthesis cover for a leg prosthesis made of a foam material or a rubber material. A reinforcement of the material in the zones which are particularly exposed to load does not lead to improved durability; moreover, thick cosmetic covers influence flexion-related and extension-related behavior of the prosthetic joints.

SUMMARY

It is, therefore, an object of the present invention to provide a cosmetic prosthetis cover in which has no or only a slight influence on the functionality of the prosthesis and, moreover, ensures greater durability. This is achieved, according to the invention, by a cosmetic prosthesis cover having the features of the main claim. Advantageous embodiments and refinements of the invention are disclosed in the dependent claims, the description and in the figures.

The cosmetic prosthetis cover for covering a prosthesis, according to the invention, having a distal portion and a joint portion which, in the fitted state of the cosmetic prosthesis cover covers a joint unit which is disposed between a proximal prosthetic component and a distal prosthetic component, provides that the joint portion is configured from a 3D spacer warp-knit which has an upper textile and a lower textile, which are affixed to one another in a spaced-apart manner by support threads.

On account of the embodiment of the joint region in the cosmetic prosthesis cover from a 3D spacer warp-knit, it is possible to allow necessary expansion and compression of the cosmetic prosthesis cover in the region of the joint units, for example in the region of the knee or of the elbow, without any influence on functionality being exerted on the prosthetic knee joint. 3D spacer warp-knits having an upper textile and a lower textile enable a high degree of deformation without strong forces being required for deformation. On account thereof, functionality of the prosthesis, which is regularly adjusted and adapted to the patient without the cosmetic prosthesis cover being fitted, is not or only minimally influenced. Moreover, at a low weight, a large volume is occupied by the spacer warp-knit, with good dimensional stability and, at the same time, great elasticity being achieved. Knits, wovens, scrims and warp-knits, which are composed of a fiber composite, are considered as upper and lower textiles.

The joint portion may be fastened on the distal portion, such that a modular construction of the cosmetic prosthesis cover is made possible. The distal portion covers, for example, the lower-leg tube or the lower-leg prosthesis and, if applicable, parts of the prosthetic foot, while the joint portion adjoins the proximal end of the distal portion. The joint portion, with its proximal end, may be directly fastened on a proximal prosthetic component or be designed so as to bear thereon; for example, the joint portion may be directly fastened on a thigh socket or an upper-arm socket, in particular where the upper-arm socket or thigh socket has a corresponding contour, such that an almost offset-free transition can be produced.

The joint portion may be adhesively bonded, welded, stitched, hook-and-loop fastened to or foamed onto the distal portion, such that a material-integral or form-fitting connection between the joint portion and the distal portion can be produced. The joint portion may be affixed on the proximal prosthetic component by form-fitting elements or by adhesive bonding or similar. It is likewise possible for the joint portion to be fastened on the distal portion and/or proximal portion by way of magnetic holders or, in a clamping manner, by way of a force-fit.

The distal portion may be configured from a foam material which, as a preformed block, is adapted to the prosthetic unit by an orthopedic technician and is modulated, for example according to the ideal of the untreated leg, such that a symmetrical appearance can be achieved. As an alternative to a foam material, the distal portion may also be made of a thin, smooth-walled plastic material which may be affixed on the distal prosthetic component by way of suitable spacer elements and fastening units.

The joint portion may have a closed cross section, such that it may be configured as a tubular component part. The closed cross section may be produced by way of a corresponding manufacturing method of the 3D spacer warp-knit; alternatively, sewing, adhesive bonding or welding a planar blank of the 3D spacer warp-knit is possible and provided. As an alternative to a durable, closed cross-sectional shape, releasable closure units may also be provided on the joint portion, for example hook-and-loop fasteners, hooks or similar, such that an individual adaption of the circumference of the joint portion is possible in a simple manner.

The distal portion of the cosmetic prosthesis cover, at least across part of its longitudinal extent or across its entire longitudinal extent, may have an open cross section, such that the distal portion may be bent open and be placed over the distal prosthetic component. A cavity for receiving the prosthetic unit is configured within the cosmetic prosthesis cover. The cavity may be configured in the joint portion or also in the distal portion. A recess, through which access from the outside to the joint unit lying in a covered and protected manner may be accomplished, may be configured in the joint portion. On account thereof, it is possible for the prosthetic unit to be adjusted without taking off the cosmetic prosthesis cover.

The cosmetic prosthesis cover, moreover, may be provided with a casing of an elastic material, in particular for achieving a smooth surface which is similar to the impression of a natural leg. The elastic casing may be composed of a textile or a foam material and, on account of the high elasticity, has no or only a minimal adverse effect on functionality.

The distal portion has a contour which is adapted to the shaping of the natural limb. The cosmetic prosthesis cover may be configured as a covering for a prosthetic leg and have a preformed patella region or a patella insert, such that a shaped design which approximates the natural appearance in the case of both an extended prosthetic leg and also a flexed prosthetic leg is achieved. The patella insert may be composed of a 3D spacer warp-knit or another material.

Apart from a distal portion, a proximal portion, which may be fastened on the joint portion, may also be provided. The proximal portion of the cosmetic prosthesis cover adjoins the proximal end of the joint portion and, for example, can be pulled over an upper-arm stump or thigh stump, in order to produce there a smooth surface or a harmonization with the shape of the untreated thigh lying opposite thereof. The proximal portion may be configured in an analogous manner to the distal portion, for example from a plastic material or a foam material. The proximal portion, across at least part of its longitudinal extent, may likewise have an open cross section. A recess in the shape of a wedge, for example, into which variously sized inserts can be inserted in order to make possible a circumferential adaptation of the proximal portion, may be configured in the proximal portion. In an analogous manner to the distal portion, the joint portion may be adhesively bonded, welded, stitched, hook-and-loop fastened to or foamed onto the proximal portion. Apart from a permanent connection, the joint portion may also be releasably fastened on the proximal portion; fastening by way of force-fitting is likewise possible and provided.

A refinement of the invention provides that the joint portion may be fastened on the joint component, such that a direct assignment of the joint portion to the joint component may take place. It is, therefore, possible, in principle, that the covering portions of the cosmetic prosthesis cover are separately fastened on the prosthetic components, without being connected to one another. There is, however, also the possibility for the joint portion to be fastened on the distal portion and/or the proximal portion, wherein these portions may likewise be fastened on the proximal and distal prosthetic components.

BRIEF DESCRIPTION OF THE DRAWINGS

In the following, exemplary embodiments of the invention will be described in more detail by means of the appended figures. In the figures:

FIG. 8 shows an individual view of a joint region;

FIG. 9 shows an individual view of a connection element between a joint region and a proximal portion;

FIG. 10 shows an alternative fastening possibility of the joint portion on a proximal portion or distal portion;

FIGS. 11a to 11b show an illustration of the volumetric adaptation; and

DETAILED DESCRIPTION

Figure 1:
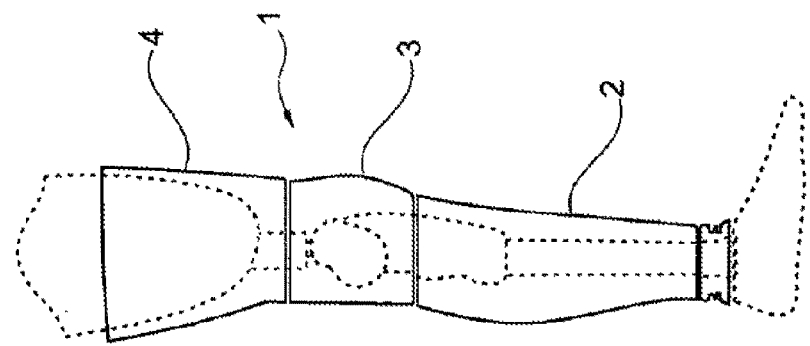
FIG. 1 shows a schematic view of a cosmetic prosthesis cover in the fitted state, having a covering.

In FIG. 1, a cosmetic prosthesis cover 1 is illustrated in a fitted state on a prosthesis 10 which is configured as a prosthetic leg. The prosthesis 10 has a distal component 20 in the form of a lower-leg tube having a prosthetic foot fastened thereon, a prosthetic knee joint 30 and a proximal prosthetic component 40 in the form of a thigh stump. The proximal component 40 is connected in an articulated manner to the distal component 20 via the prosthetic knee joint 30.

The cosmetic prosthesis cover 1, which has shaping components, is fitted about the prosthesis 10. A distal portion 2, which has the external shape of a natural calf, is disposed about the distal prosthetic component 20. A joint portion 3, which is situated in the region of a natural knee joint and is disposed about the pivot axis (not drawn) of the prosthetic knee joint 30, is disposed above, i.e. proximally to the distal portion 2. The joint portion 3 completely shrouds the region about the joint axle of the prosthetic knee joint 30 and extends in a proximal and distal manner to the joint axle. The proximal portion 4, which forms the transition from the joint region 3 to the thigh socket 40, is proximally disposed to the joint portion 3. The proximal portion 4 reproduces the contour of a natural thigh and serves to achieve a transition which is as inconspicuous as possible from the thigh stump 40 to the joint portion 3. The portions 2, 3, 4 of the cosmetic prosthesis cover 1, which are disposed above one another, collectively reproduce an approximate external contour of a natural leg. A casing 6 of a highly elastic material, for example a highly elastic textile, is disposed on the outer side of the portions 2, 3, 4, in order to achieve a closed surface for a harmonic overall impression and, moreover, to conceal transitions between the individual portions 2, 3, 4.

The joint region 3 is configured from a 3D spacer warp-knit and has an upper textile, a lower textile and support threads which fasten the upper textile and the lower textile to one another in a spaced-apart manner. The support threads may be configured from another material than the upper textile and the lower textile; likewise, the upper textile may be made from different materials in order to make possible an adaptation to the desired properties.

Figure 2:
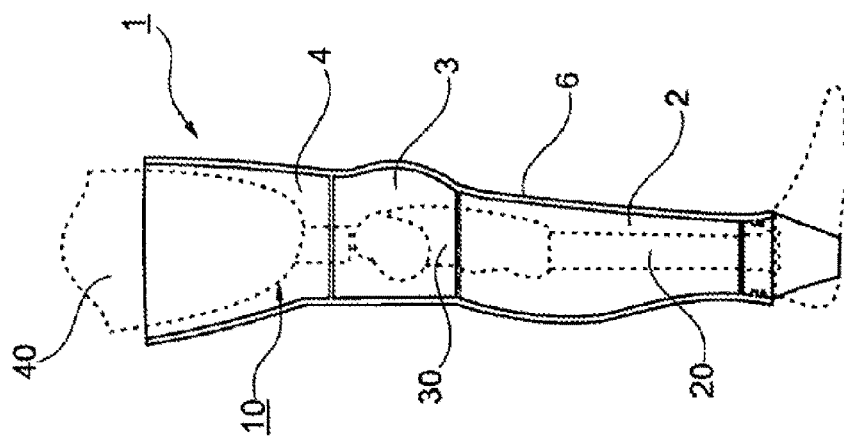
FIG. 2 shows an embodiment according to FIG. 1, without a covering.

In FIG. 2, the cosmetic prosthesis cover 1 is shown without the casing 6. The individual portions 2, 3, 4 are configured as modular components and may be individually affixed on the prosthesis 10. A bridging element for connection to the prosthetic foot is illustrated below the distal portion 2.

Figure 3:
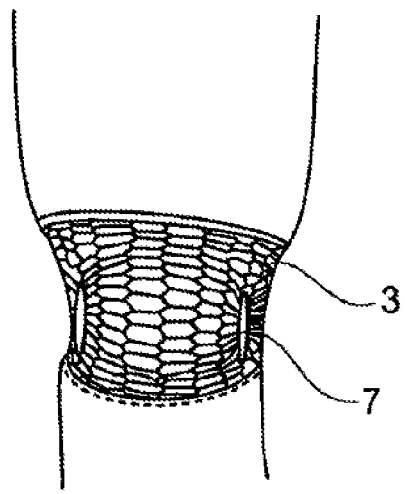
FIG. 3 shows a detailed view of a joint region.

The joint portion 3 from the 3D spacer warp-knit, in the illustrated extended position, frontally has a patella bulge which is configured approximately according to the patella of a natural leg. The joint portion 3 is configured so as to be tubular and, with its distal end and its proximal end, is connected to the respectively adjoining portions 3, 4. In FIG. 3, a frontal view of the joint portion 3 is illustrated in an individual illustration, by means of which the honeycomb-like structure of the upper textile of the 3D spacer warp-knit can be identified. A preformed patella region 7 is configured by shortening lateral regions of the joint portion 3, such that restrictions, which cause a shape of the joint region 3 which approximates the natural shape, result on both sides of a vertically running center plane (not illustrated). The restrictions 7 may be configured by stitchings or similar.

Figure 4:
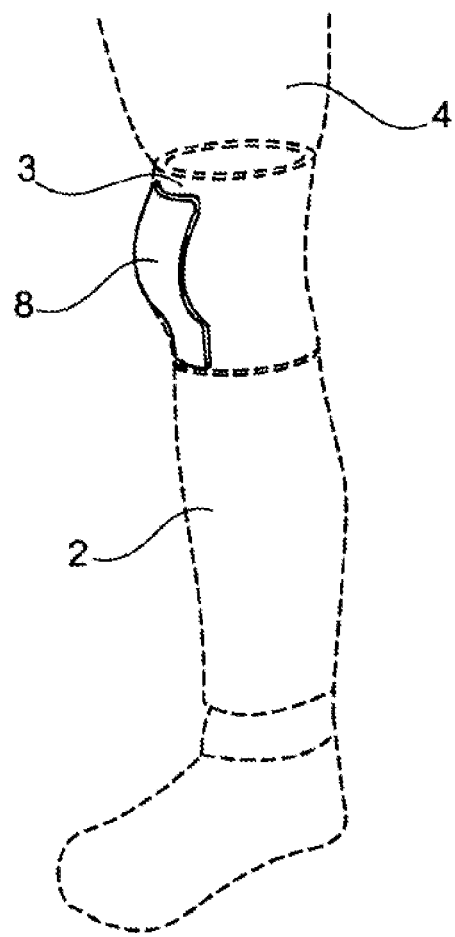
FIG. 4 shows a joint region having a patella insert.

A variant of the invention in which the distal portion 2 and the proximal portion 4 are only alluded to is illustrated in FIG. 4. A patella insert 8 of an elastic, flexible material, for example a 3D spacer warp-knit which, on account of a coating, of the employment of other materials or of other thread arrangements, has higher strength and dimensional stability, in comparison to the remaining 3D spacer warp-knit, is inserted into the joint portion 3, such that flexion of the prosthetic knee joint is indeed readily possible, but the shape of the patella in the frontal region remains alluded to. Alternatively, the patella insert 8 may be configured as an insert in the shape of a spoon which is fastened on the distal portion 2. The insert is situated behind the 3D spacer warp-knit and configures a patella. Preferably, during flexion and extension, the insert elastically rebounds and, on account of the bearing force, reproduces the patella.

Figure 5:
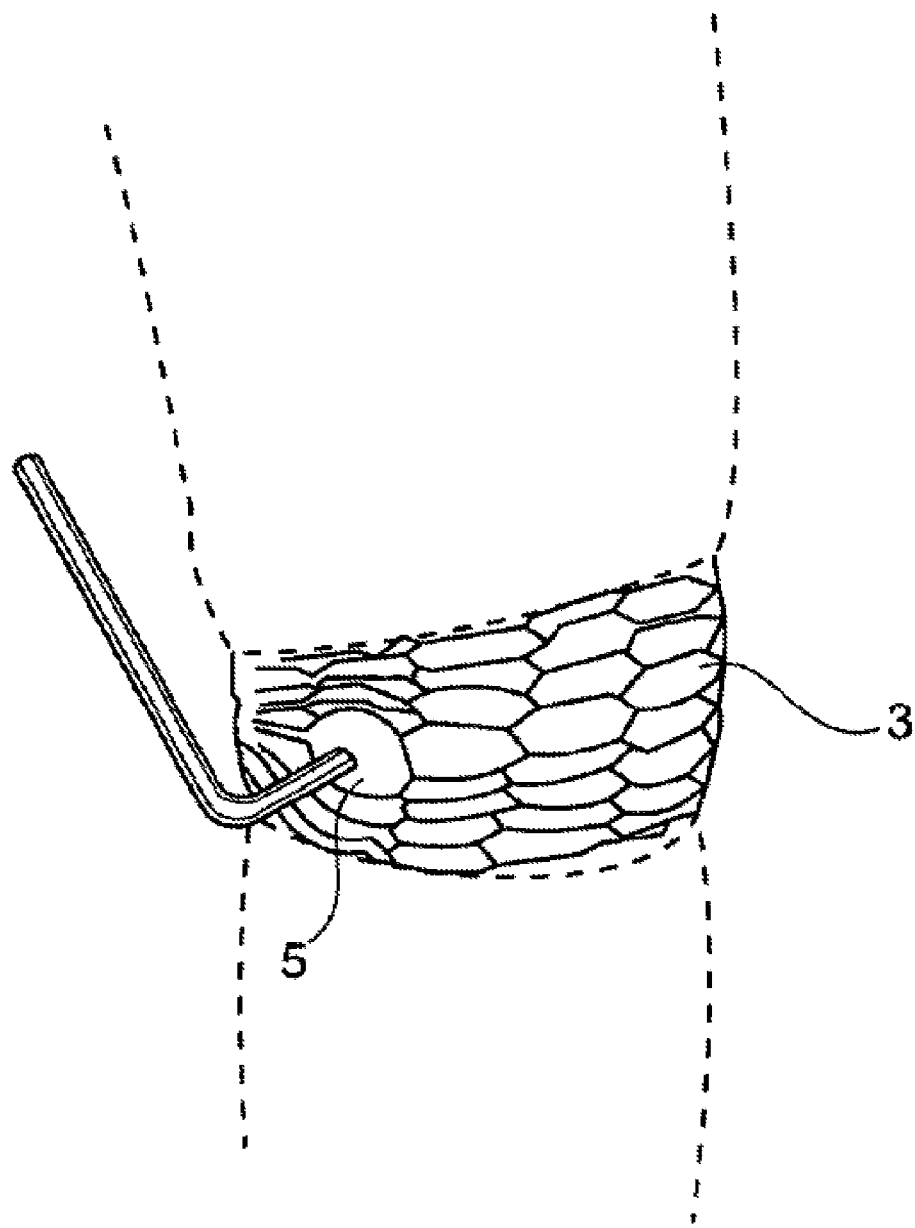
FIG. 5 shows a perspective detailed view of a variant of a joint region.

In FIG. 5, a perspective view of the joint portion 3 having a recess 5 in the medial or lateral region is illustrated. On account of the recess 5, a tool may be introduced by way of which the prosthetic joint 30 can be adjusted and adapted to the respective user.

Figure 6:
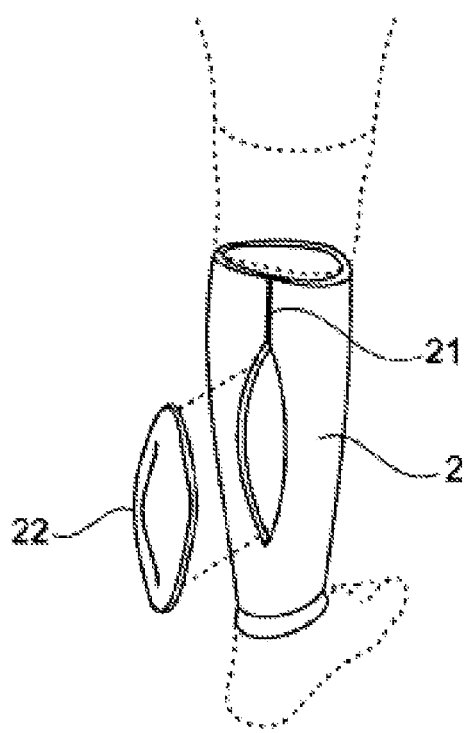
FIG. 6 shows an individual view of a distal portion.

In FIG. 6, a perspective rear view of the distal portion 2 is illustrated. It can be identified that a slot 21 extends across a partial length of the distal portion 2, such that a partially open hollow cross section is formed. An insert 22 can be introduced into the rearward region, in order to configure various circumferences of the distal portion 2, such that a more simple adaptation to diverse shape designs can be achieved, even in the case of an embodiment of the distal portion 2 from a thin-walled material, for example a thin-walled foam material or an elastic material.

Figure 7:
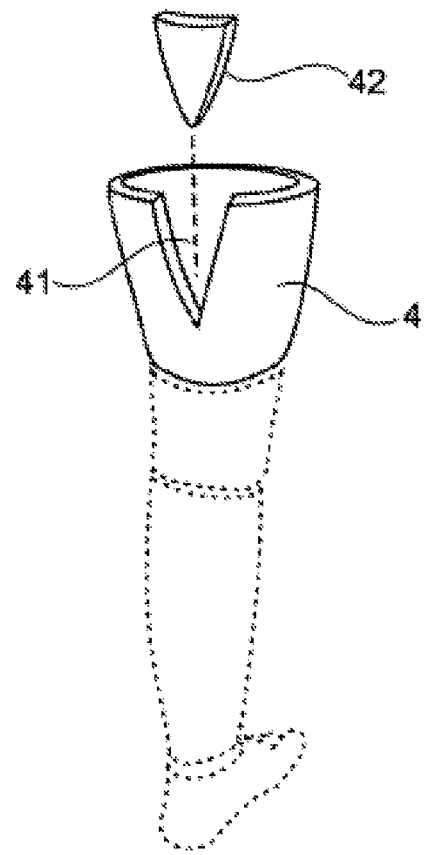
FIG. 7 shows a detailed view of a proximal portion.

FIG. 7 shows an individual illustration of the proximal portion 4 having a wedge-shaped recess 41 in the rearward region, which is configured in order to receive an insert 42. Here too, a partially open cross section is configured across the longitudinal extent of the proximal portion 4. An adaptation to the circumference desired in each case may likewise be achieved by way of the inserts 42. Apart from the exemplary embodiments for a covering of a prosthetic leg shown in FIGS. 6 and 7, volumetric adaptation of the cosmetic covers may also take place by way of inserts in other prosthetic units, for example in arm prostheses. Here too, by way of targeted incorporation of recesses and filling with inserts of various sizes, various cosmetic-cover volumes may be implemented. The larger the insert in the case of a constant size of the recesses, the larger the volume of the adapted cosmetic prosthesis cover, wherein the insert preferably terminates flushly with the remaining cosmetic prosthesis cover and the material thickness of the inserts substantially corresponds to the material thickness of the remaining cosmetic prosthesis cover.

In FIG. 8, an individual illustration of the joint portion 3 is shown. The hollow-body like, tube-like embodiment of the joint portion 3, having a closed cross section, can be identified. Likewise, the patella bulge in the front region can be seen. The tubular joint portion 3 has a material thickness which substantially corresponds to the material thickness of the distal and proximal portions 2, 4 in the adjoining region, such that a ready assignment of the respective portions 2, 3, 4 to one another can take place. A sufficiently large cavity to enable free movement of the prosthetic joint is available in the interior of the joint portion 3.

In FIG. 9 a fastening possibility of the joint portion 3 on the distal portion 2 and the proximal portion 4 is shown. Two connection tapes 32, 34 are fastened on the joint portion 3 and have a groove and a recess into which the respective adjoining portion 2, 4 is introduceable. The respective portion 2, 3 may be adhesively bonded, stitched, hook-and-loop fastened, clamped or welded in the groove.

An alternative fastening in which the fastening tapes 32, 34 are only disposed and fastened on the outer circumference of the respective portions 2, 3, 4 is shown in FIG. 10. The fastening tapes 32, 34 may be configured as adhesive tapes, hook-and-loop tapes or a combination thereof.

A distal portion 2 is shown in a perspective illustration in FIG. 11a. The distal portion 2 is configured as a basic body which is supplied pre-fabricated. The distal portion 2 is configured as a hollow body, in the cavity of which a lower-leg tube for connecting a prosthetic knee joint with a prosthetic foot may be accommodated. Further components of the prosthetic aid may likewise be disposed in the cavity. The external shape of the distal portion 2 corresponds to that of a natural lower leg, wherein dimensioning which covers as large a range of variations as possible is preferably chosen. A plurality of basic bodies of the distal portion 2 having different sizes may also be offered, such that corresponding distal portions 2 can be made and adapted for small, medium and large patients having different calf diameters. As a first step for adaptation, an adjustment of the length of the distal portion 2 is performed. For example, an orthopedic technician may perform a corresponding shortening on the distal end of the distal portion 2 such that the distal portion 2 is adapted to the requirements.

After the length adaptation as illustrated in FIG. 11a, volumetric adaption may take place. This takes place in that material is cut out from the distal portion 2, such that a recess 41 is produced. In the exemplary embodiment illustrated, a longitudinal slot is first introduced into the distal portion 2 across its entire length, such that an altogether open cross section is formed. The longitudinal slot is subsequently widened, such that a lenticular or drop-shaped recess 41 is configured in the distal portion 2 which may be configured from a foam in a different plastic. Widening typically takes place by way of material removal and by bending open the basic body. A correspondingly contoured insert 42 is inserted into this recess 41 and connected, for example adhesively bonded or welded, along the lateral edges of the recess 41. A plurality of inserts 42, which in each case have a different volume, are shown in the upper illustration of FIG. 11b. On account of the employment of a larger insert 41, i.e. the left insert 42 in FIG. 11b, a larger volume of the distal portion 2 can be implemented; if only a comparatively slight volumetric enlargement of the distal portion 2 is to take place, the right insert 42 is inserted into the recess 41 and connected to the remaining material.

The lower illustration of FIG. 11b shows a cross-sectional view, wherein the cross section is positioned approximately mediately on the distal portion 2. The recess 41, into which the insert 42 is inserted, can be identified next to the distal portion 2 and the cavity. Adhesive bonding or welding of the insert 42 to the remaining distal portion 2 has not yet taken place. As can be seen from the cross-sectional illustration, the left insert 42 is not only larger with respect to its circumference, but also its volume, that is to say that the appendage 42 has a larger wall thickness. On account of the individual embodiment of the inserts 42, it is possible to select from a preformed contingent of inserts 42 and to achieve an embodiment of the distal portions 2 which corresponds to the shapes of the contralateral, i.e. untreated leg.

Figure 12A:
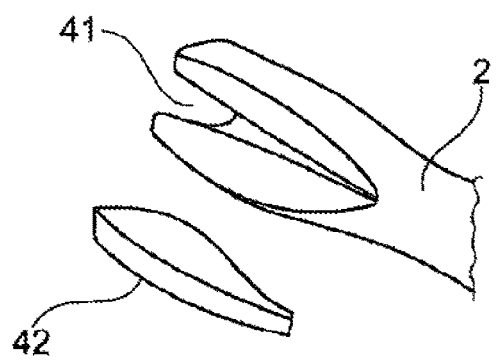
FIGS. 12a to 12c show a variant of FIGS. 11a-b.
Figure 12B:
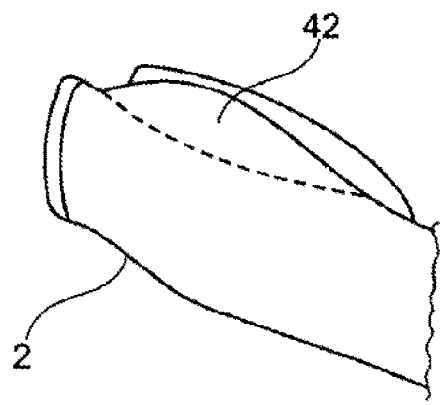
Figure 12C:
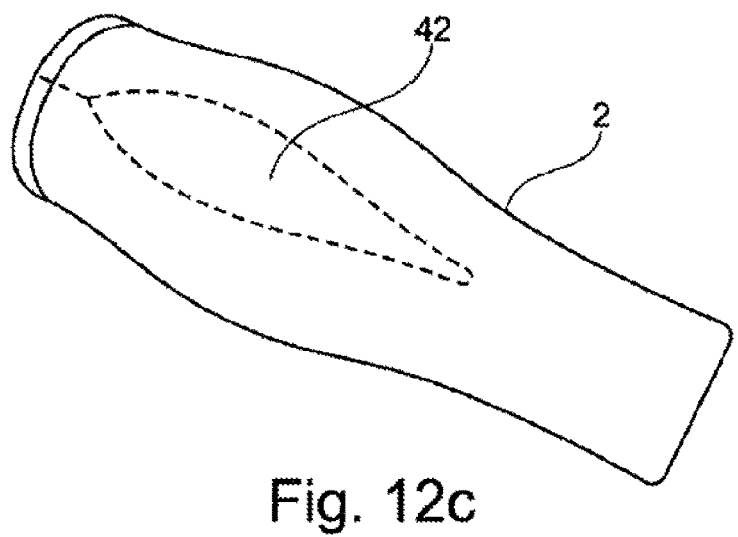

A variant of the volumetric adaptation is illustrated in FIGS. 12a to 12c. In FIG. 12a, the distal portion having the recess 41 is configured in the form of an insection which does not extend across the entire longitudinal extent of the distal portion 2. The insert 42, which is to be inserted into the recess 41 for the volumetric adaption, lies next to the distal portion 2. An intermediate step in the volumetric adaptation, in which the insert 42 is already fastened, for example welded or adhesively bonded, on one side of the recess 41 on the distal portion 2, can be seen in FIG. 12b. The completed distal portion 2, in which the insert 42 has been completely incorporated in the distal portion 2, can be seen in FIG. 12c. Any potential protrusions have been smoothed, such that a smooth, substantially edgeless surface of the distal portion 2 can be implemented.

The volumetric adaptation according to the explanations pertaining to FIGS. 6, 7, 11a to 11b and 12a to 12c may also be performed separately, without a proximal portion and/or a joint portion having to be fastened on the distal portion 2. Such a procedure applies when a prosthetic unit does not have to be covered in the knee region or when it is only a lower-leg prosthesis. The same may also be carried out for other extremities, for example for the volumetric adaptation of coverings on thighs or arm prostheses. On account of the presented method it is possible to provide an individualizable cosmetic prosthesis cover having additional volumetric elements in the form of inserts 42 for manufacturing a cosmetic covering for prostheses. Simple individualization to the desired patient measurements is possible by way of a parts-bin system which, apart from basic bodies, also has various sizes of inserts 42 which can then be adapted to the respective patient. On account thereof, it is possible for a more rapid adaptation and a more cost-effective manufacturing of a cosmetic prosthesis cover to be implemented. The inserts 42 may have different shapes; they advantageously have a similar contour, such that the recesses 41 substantially follow said contours, wherein consideration is made for the desired increase in volume. The inserts 42, like the basic bodies, are pre-fabricatable on an industrial scale, such that the moldings can easily be tailored for adaptation of the cosmetic prosthesis cover to the respective patient. On account thereof, manufacturing a cosmetic garment for a prosthetic unit is simplified. The completed cosmetic prosthesis cover can then still be provided with a casing, for example a stocking-like fabric, such that a uniform coloring and a skin-like surface structure can be achieved.

The invention claimed is:

1. A cosmetic prosthesis cover for covering a prosthesis, the prosthesis having a proximal prosthetic component, a distal prosthetic component, and a joint unit disposed between the proximal and distal prosthetic components, the cosmetic prosthesis cover comprising:
   a distal portion forming a hollow cavity configured to receive the distal prosthetic component, the hollow cavity formed along an entire longitudinal extent of the distal portion when covering the distal prosthetic component in a fitted state;
   a joint portion separate from the distal portion and positioned proximal of the distal portion, the joint portion being configured to cover the joint unit when the cosmetic prosthesis cover is in the fitted state, the joint portion being formed from a 3D spacer warp-knit having an upper textile and a lower textile;
   support threads configured to connect the upper and lower textiles to each another in a spaced-apart manner; and
   hook-and-loop fasteners, the joint portion being coupled to the distal portion with the hook-and-loop fasteners.

2. The cosmetic prosthesis cover as claimed in claim 1, wherein the distal portion comprises a foam material.

3. The cosmetic prosthesis cover as claimed in claim 1, wherein the joint portion is tubular shaped and has a closed cross section.

4. The cosmetic prosthesis cover as claimed in claim 1, wherein the distal portion has an open cross section across at least part of its length in an unassembled configuration.

5. The cosmetic prosthesis cover as claimed in claim 1, wherein the joint portion defines a cavity configured to receive the prosthesis.

6. The cosmetic prosthesis cover as claimed in claim 1, wherein the joint portion comprises a recess.

7. A cosmetic prosthesis cover for covering a prosthesis, the prosthesis having a proximal prosthetic component, a distal prosthetic component, and a joint unit disposed between the proximal and distal prosthetic components, the cosmetic prosthesis cover comprising:
  a distal portion forming a hollow cavity configured to receive the distal prosthetic component, the hollow cavity formed along an entire longitudinal extent of the distal portion when covering the distal prosthetic component in a fitted state;
  a tubular shaped joint portion separate from the distal portion and positioned proximal of the distal portion, the joint portion, in the fitted state of the cosmetic prosthesis cover, being configured to extend around an entire circumference of the joint unit from a distal end of the joint unit to a proximal end of the joint unit, wherein the joint portion is formed from a 3D spacer warp-knit which has an upper textile and a lower textile, the upper and lower textiles being affixed to one another in a spaced-apart manner by support threads; and
  hook-and-loop fasteners, the joint portion being coupled to the distal portion with the hook-and-loop fasteners.

8. The cosmetic prosthesis cover as claimed in claim 7, wherein the distal portion is formed from a foam material.

9. The cosmetic prosthesis cover as claimed in claim 7, wherein the joint portion has a closed cross section.

10. The cosmetic prosthesis cover as claimed in claim 7, wherein the distal portion, at least across part of its longitudinal extent, has an open cross section in an unassembled configuration.

11. The cosmetic prosthesis cover as claimed in claim 7, wherein the joint portion defines a cavity for receiving the prosthesis.

12. The cosmetic prosthesis cover as claimed in claim 7, wherein a recess is formed in the joint portion.

13. The cosmetic prosthesis cover as claimed in claim 7, further comprising a casing formed of an elastic material.

14. The cosmetic prosthesis cover as claimed in claim 7, further comprising a patella insert.

15. The cosmetic prosthesis cover as claimed in claim 7, further comprising a proximal portion which is fastened on the joint portion.

16. The cosmetic prosthesis cover as claimed in claim 7, wherein the joint portion is configured to be fastened on the joint unit.

* * * * *